US010302774B2

(12) United States Patent
Bures et al.

(10) Patent No.: US 10,302,774 B2
(45) Date of Patent: May 28, 2019

(54) DETECTOR ASSEMBLY FOR USE IN CT IMAGING SYSTEMS

(71) Applicant: Morpho Detection, LLC, Newark, CA (US)

(72) Inventors: Brian Lee Bures, Pelham, NH (US); Samit Kumar Basu, Fremont, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 61 days.

(21) Appl. No.: 15/137,763

(22) Filed: Apr. 25, 2016

(65) Prior Publication Data

US 2017/0307765 A1 Oct. 26, 2017

(51) Int. Cl.
*G01T 1/20* (2006.01)
*G01N 23/046* (2018.01)

(52) U.S. Cl.
CPC ......... *G01T 1/2018* (2013.01); *G01N 23/046* (2013.01); *G01T 1/2002* (2013.01); *G01N 2223/505* (2013.01)

(58) Field of Classification Search
CPC .................................................. G01T 1/2018
See application file for complete search history.

(56) References Cited

U.S. PATENT DOCUMENTS

| 5,956,382 | A | 9/1999 | Wiener et al. |
| 6,559,452 | B1 | 5/2003 | Tashiro |
| 6,627,896 | B1 | 9/2003 | Hlavenka et al. |
| 6,750,456 | B1* | 6/2004 | Majewski ............. G01T 1/1644 250/366 |
| 7,626,176 | B2 | 12/2009 | Zeitler et al. |
| 7,787,928 | B2 | 8/2010 | Frisch et al. |
| 8,735,849 | B2 | 5/2014 | Hlavenka et al. |
| 9,153,416 | B2 | 10/2015 | Hlavenka et al. |
| 2007/0138380 | A1* | 6/2007 | Adkisson .................. G01J 1/04 250/227.11 |
| 2008/0073542 | A1* | 3/2008 | Siegel ................... G01T 1/1644 250/368 |

(Continued)

FOREIGN PATENT DOCUMENTS

| CN | 102331599 A | 1/2012 |
| WO | 2003096070 A1 | 11/2003 |

OTHER PUBLICATIONS

Extended European Search Report, Application No. 17000690.2-1559, dated Sep. 22, 2017, 10 pps.

*Primary Examiner* — Edwin C Gunberg
(74) *Attorney, Agent, or Firm* — Armstrong Teasdale LLP

(57) ABSTRACT

A detector assembly for a CT imaging system is provided. The detector assembly including a scintillator block including a plurality of pixels, each pixel configured to receive x-ray beams travelling in a transmission direction, a plurality of photodiodes, and a light guide coupled between the scintillator block and the plurality of photodiodes, the light guide including a plurality of light pipes, each light pipe configured to guide light emitted from a pixel of the plurality of pixels into an associated photodiode of the plurality of photodiodes, wherein each pixel has a first cross-sectional area that is substantially perpendicular to the transmission direction, wherein each photodiode has a second cross-sectional area that is substantially perpendicular to the transmission direction, and wherein the first cross-sectional area is different from the second cross-sectional area.

19 Claims, 6 Drawing Sheets

(56) References Cited

U.S. PATENT DOCUMENTS

| | | |
|---|---|---|
| 2009/0146070 A1 | 6/2009 | Vieira Da Rocha et al. |
| 2011/0017916 A1 | 1/2011 | Schulz et al. |
| 2016/0187496 A1* | 6/2016 | Bradford ............... G01T 1/2985 |
| | | 250/366 |

* cited by examiner

DETECTOR ASSEMBLY FOR USE IN CT IMAGING SYSTEMS

BACKGROUND

The embodiments described herein relate generally to CT imaging systems, and more particularly, to detector assemblies for CT imaging systems.

In some computed tomography (CT) imaging systems, an x-ray source projects a fan-shaped beam which is collimated to lie within an X-Y plane of a Cartesian coordinate system and generally referred to as an "imaging plane". The x-ray beam passes through an object being imaged. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam intensity at each detector location. The intensity measurements from all the detectors are acquired separately to produce a transmission profile and reconstruct an image of the object.

Detector assemblies for at least some known CT imaging systems include an array of tightly packed pixels in a scintillator and a corresponding array of diodes. The area of the pixel array typically matches the area of the diode array, which may require manufacturing custom silicon diodes to match the dimensions of the pixels. Accordingly, using diodes that are matched to the dimensions of the pixels may be relatively expensive.

BRIEF SUMMARY

In one aspect, a detector assembly for a CT imaging system is provided. The detector assembly including a scintillator block including a plurality of pixels, each pixel configured to receive x-ray beams travelling in a transmission direction, a plurality of photodiodes, and a light guide coupled between the scintillator block and the plurality of photodiodes, the light guide including a plurality of light pipes, each light pipe configured to guide light emitted from a pixel of the plurality of pixels into an associated photodiode of the plurality of photodiodes, wherein each pixel has a first cross-sectional area that is substantially perpendicular to the transmission direction, wherein each photodiode has a second cross-sectional area that is substantially perpendicular to the transmission direction, and wherein the first cross-sectional area is different from the second cross-sectional area.

In another aspect, a light guide for use in a CT imaging system is provided. The light guide includes a plurality of light pipes extending from a first end of the light guide to a second end of the light guide, wherein at the first end, each light pipe of the plurality of light pipes has a first cross-sectional area that is substantially equal to a cross-sectional area of a corresponding pixel, wherein at the second end, each light pipe has a second cross-sectional area that is substantially equal to a cross-sectional area of a corresponding photodiode, and wherein the first cross-sectional area is different from the second cross-sectional area.

In yet another aspect, a method of assembling a detector assembly for use in a CT imaging system sis provided. The method includes coupling a light guide to a scintillator block that includes a plurality of pixels, wherein each pixel is configured to receive x-ray beams travelling in a transmission direction, and coupling a plurality of photodiodes to the light guide, wherein the light guide includes a plurality of light pipes each configured to guide light emitted from a pixel of the plurality of pixels into an associated photodiode of the plurality of photodiodes, wherein each pixel has a first cross-sectional area that is substantially perpendicular to the transmission direction, wherein each photodiode has a second cross-sectional area that is substantially perpendicular to the transmission direction, and wherein the first cross-sectional area is larger than the second cross-sectional area.

DETAILED DESCRIPTION

The systems and methods described herein provide a detector assembly for a CT imaging system. The detector assembly includes a scintillator block including a plurality of pixels. Each pixel is configured to receive x-ray beams travelling in a transmission direction. The detector assembly further includes a plurality of photodiodes, and a light guide coupled between the scintillator block and the plurality of photodiodes. Each pixel has a first cross-sectional area and each photodiode has a second cross-sectional area. The first cross-sectional area is larger than the second cross-sectional area.

Figure 1:
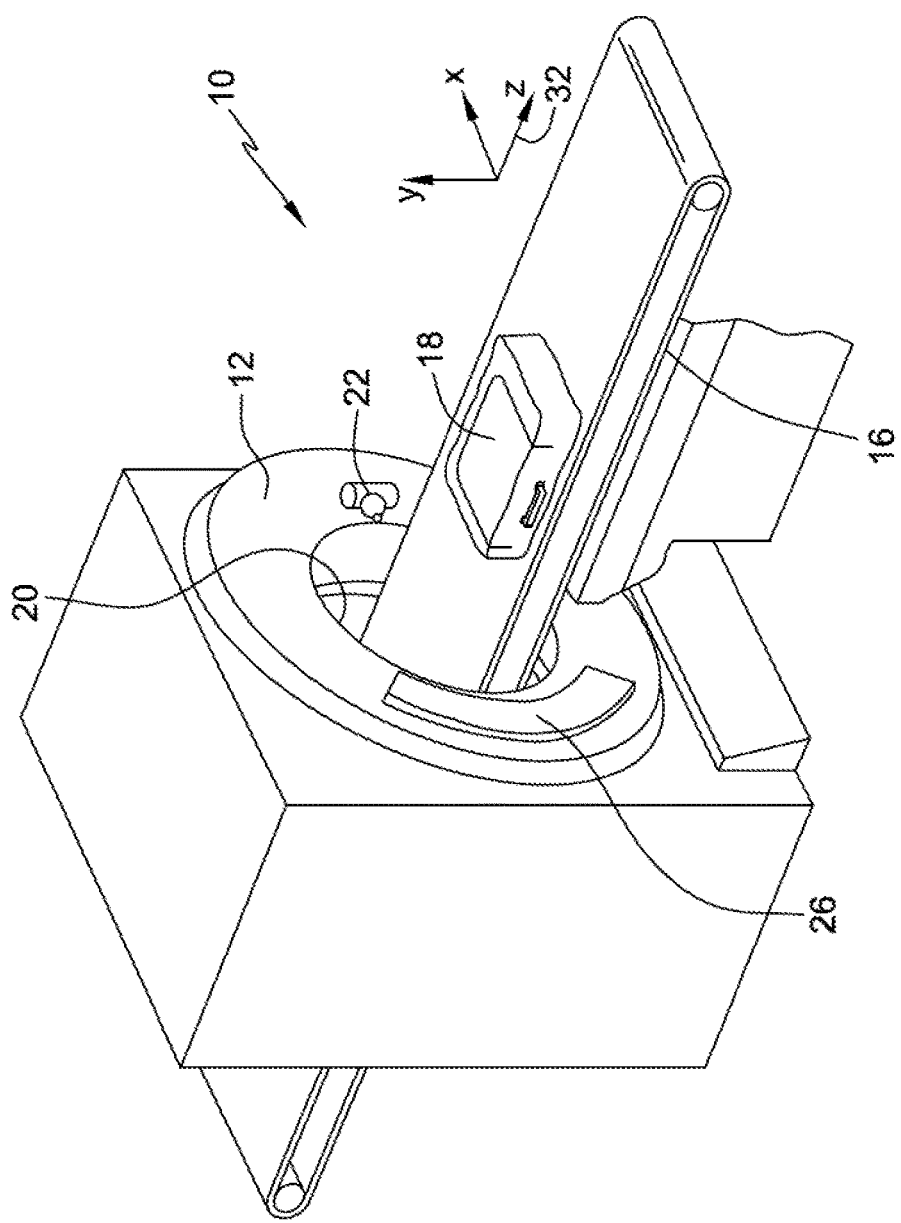
FIG. 1 is a perspective view of an exemplary CT imaging system.
Figure 2:
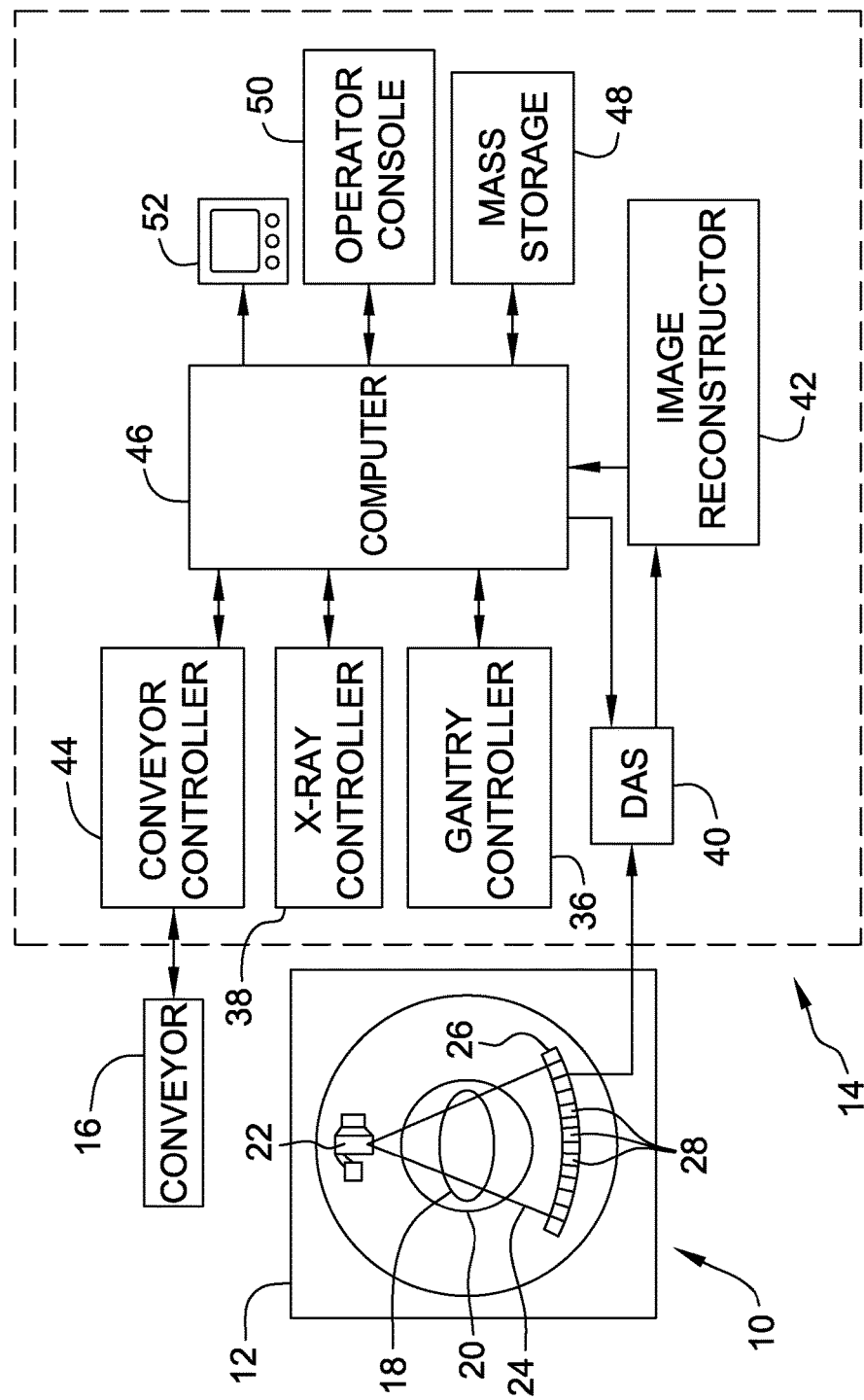
FIG. 2 is a schematic diagram of the CT imaging system shown in FIG. 1.

Referring now to FIGS. 1 and 2, a computed tomography (CT) imaging system 10 is shown. CT imaging system 10 is shown having a gantry 12, which is representative of a CT scanner, a control system 14, and a motorized conveyor belt 16 for positioning an object 18, such as a piece of luggage, in a gantry opening 20 defined through gantry 12. Gantry 12 includes an x-ray source 22 that projects a fan beam of x-rays 24 toward a detector array 26 on the opposite side of gantry 12. Detector array 26 is formed by detector elements 28, which are radiation detectors that each produce a signal having a magnitude that represents and is dependent on the intensity of the attenuated x-ray beam after it has passed through object 18 being imaged. During a helical scan that acquires x-ray projection data, gantry 12 along with the x-ray source 22 and detector array 26 rotate within an x-y plane and around object 18 about a center of rotation, while object 18 is moved through gantry 12 in a z-direction 32 perpendicular to the x-y plane of rotation. In the exemplary embodiment, detector array 26 includes a plurality of detector rings each having a plurality of detector elements 28, the detector rings having an angular configuration corresponding to x-ray source 22.

Gantry 12 and x-ray source 22 are controlled by control system 14, which includes a gantry controller 36, an x-ray controller 38, a data acquisition system (DAS) 40, an image reconstructor 42, a conveyor controller 44, a computer 46, a mass storage-system 48, an operator console 50, and a display device 52. Gantry controller 36 controls the rotational speed and position of gantry 12, while x-ray controller 38 provides power and timing signals to x-ray source 22, and data acquisition system 40 acquires analog data from detector elements 28 and converts the data to digital form for subsequent processing. Image reconstructor 42 receives the digitized x-ray data from data acquisition system 40 and performs an image reconstruction process that involves filtering the projection data using a helical reconstruction algorithm.

Computer 46 is in communication with the gantry controller 36, x-ray controller 38, and conveyor controller 44 whereby control signals are sent from computer 46 to controllers 36, 38, 44 and information is received from controllers 36, 38, 44 by computer 46. Computer 46 also provides commands and operational parameters to data acquisition system 40 and receives reconstructed image data from image reconstructor 42. The reconstructed image data is stored by computer 46 in mass storage system 48 for subsequent retrieval. An operator interfaces with computer 46 through operator console 50, which may include, for example, a keyboard and a graphical pointing device, and receives output, such as, for example, a reconstructed image, control settings and other information, on display device 52.

Communication between the various system elements of FIG. 2 is depicted by arrowhead lines, which illustrate a means for either signal communication or mechanical operation, depending on the system element involved. Communication amongst and between the various system elements may be obtained through a hardwired or a wireless arrangement. Computer 46 may be a standalone computer or a network computer and may include instructions in a variety of computer languages for use on a variety of computer platforms and under a variety of operating systems. Other examples of computer 46 include a system having a microprocessor, microcontroller or other equivalent processing device capable of executing commands of computer readable data or program for executing a control algorithm. In order to perform the prescribed functions and desired processing, as well as the computations therefore (e.g., the execution of filtered back projection, fourier analysis algorithm(s), the control processes prescribed herein, and the like), computer 46 may include, but not be limited to, a processor(s), memory, storage, register(s), timing, interrupt(s), communication interfaces, and input/output signal interfaces, as well as combinations including at least one of the foregoing. For example, computer 46 may include input signal filtering to enable accurate sampling and conversion or acquisitions of such signals from communications interfaces. As described above, exemplary embodiments can be implemented through computer-implemented processes and apparatuses for practicing those processes.

Figure 3:
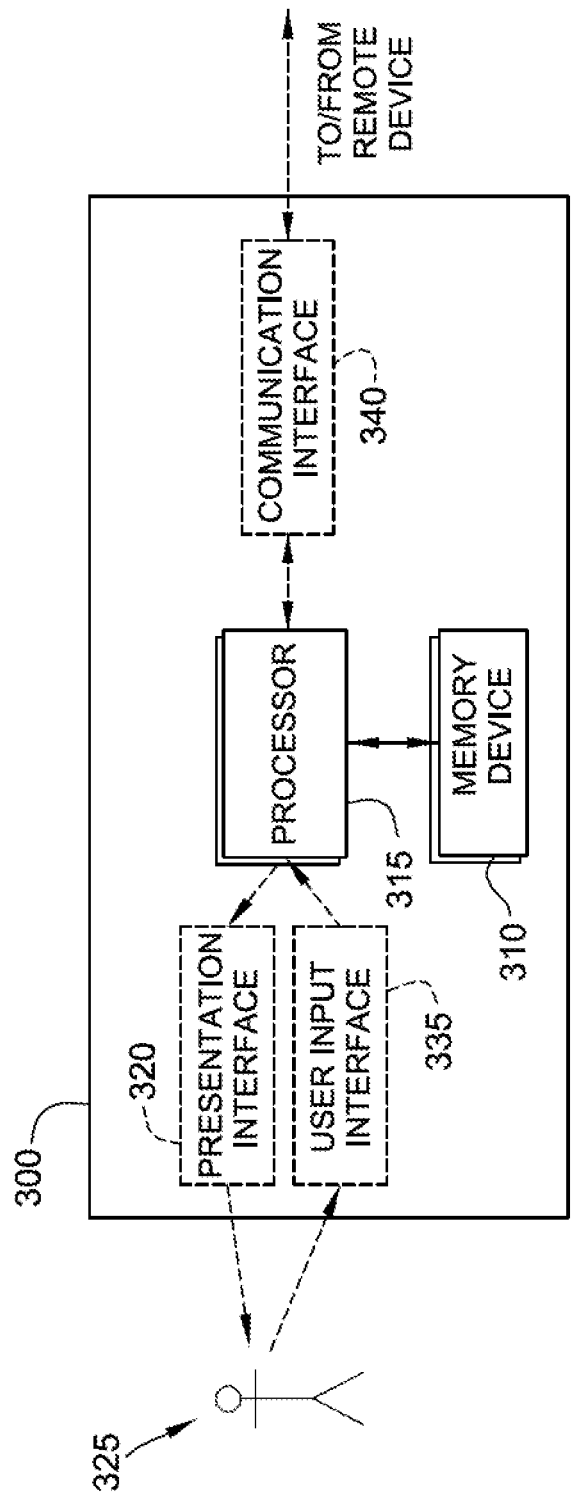
FIG. 3 is a block diagram of an exemplary computing device that may be used with the CT imaging system shown in FIGS. 1-3.

FIG. 3 is a block diagram of a computing device 300 that may be used to reconstruct an image of object 18, as described herein. Computing device 300 may be implemented as part of control system 14 or may be a separate computing device in communication with CT imaging system 10 or another imaging system. Computing device 300 includes at least one memory device 310 and a processor 315 that is coupled to memory device 310 for executing instructions. In some embodiments, executable instructions are stored in memory device 310. In the exemplary embodiment, computing device 300 performs one or more operations described herein by programming processor 315. For example, processor 315 may be programmed by encoding an operation as one or more executable instructions and by providing the executable instructions in memory device 310.

Processor 315 may include one or more processing units (e.g., in a multi-core configuration). Further, processor 315 may be implemented using one or more heterogeneous processor systems in which a main processor is present with secondary processors on a single chip. In another illustrative example, processor 315 may be a symmetric multi-processor system containing multiple processors of the same type. Further, processor 315 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), graphics processing units (GPU), and any other circuit capable of executing the functions described herein.

In the exemplary embodiment, memory device 310 is one or more devices that enable information such as executable instructions and/or other data to be stored and retrieved. Memory device 310 may include one or more computer readable media, such as, without limitation, dynamic random access memory (DRAM), static random access memory (SRAM), a solid state disk, and/or a hard disk. Memory device 310 may be configured to store, without limitation, application source code, application object code, source code portions of interest, object code portions of interest, configuration data, execution events and/or any other type of data. Further, reference templates may be stored on memory device 310.

In the exemplary embodiment, computing device 300 includes a presentation interface 320 that is coupled to processor 315. Presentation interface 320 presents information to a user 325. For example, presentation interface 320 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 320 includes one or more display devices.

In the exemplary embodiment, computing device 300 includes a user input interface 335. User input interface 335 is coupled to processor 315 and receives input from user 325. User input interface 335 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 320 and user input interface 335.

Computing device 300, in the exemplary embodiment, includes a communication interface 340 coupled to processor 315. Communication interface 340 communicates with one or more remote devices (e.g., in some embodiments, CT imaging system 10). To communicate with remote devices, communication interface 340 may include, for example, a wired network adapter, a wireless network adapter, and/or a mobile telecommunications adapter.

Figure 4:
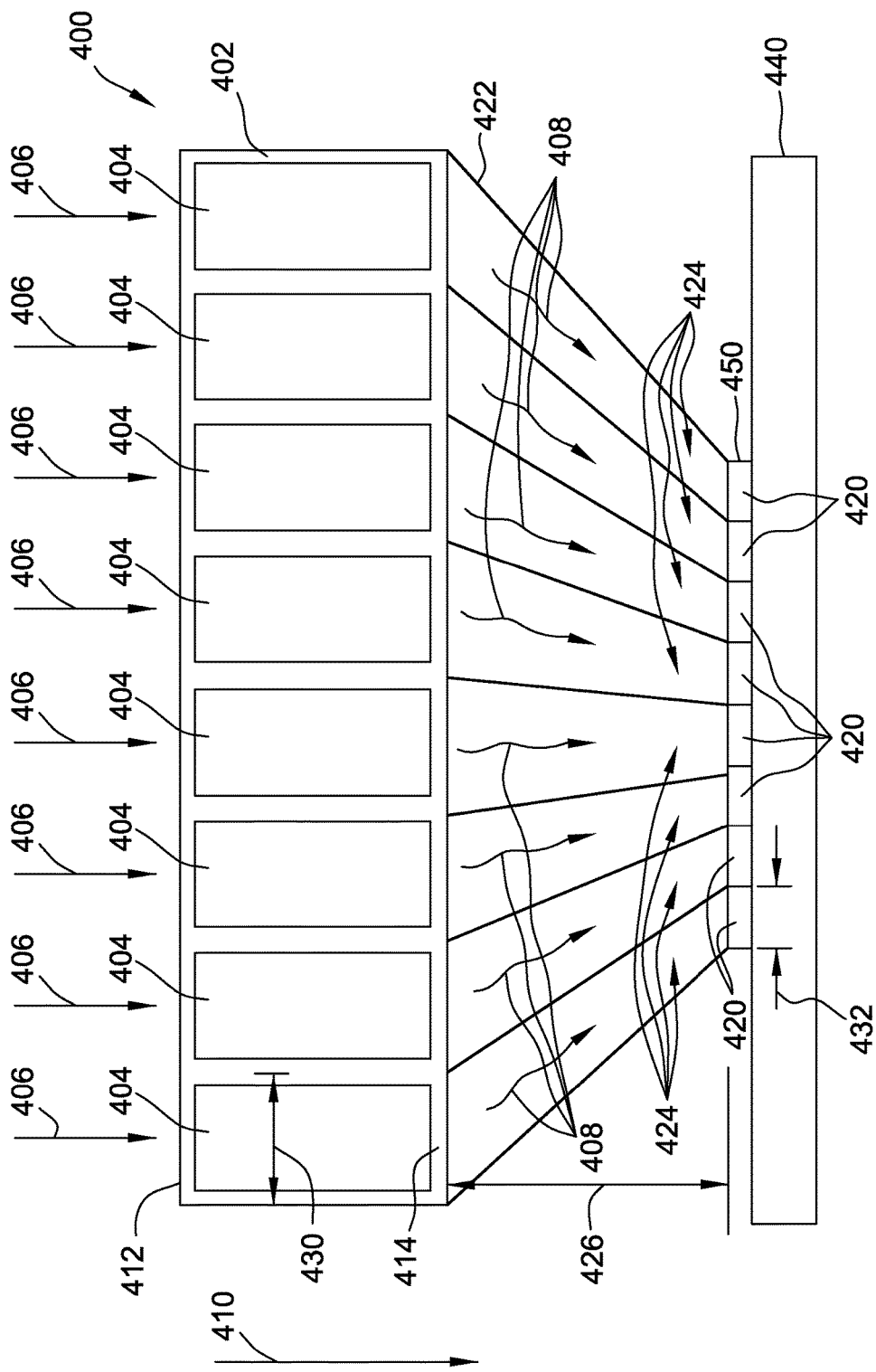
FIG. 4 is a schematic diagram of an exemplary detector assembly that may be used with the CT imaging system shown in FIG. 1.

FIG. 4 is a schematic diagram of an exemplary detector assembly 400, such as detector array 26 (shown in FIG. 1) that may be used with CT imaging system 10 (shown in FIG. 1). Detector includes a scintillator block 402 that includes a plurality of pixels 404. For clarity, only eight pixels 404 are shown in FIG. 4. However, those of skill in the art will appreciate that scintillator block 402 will generally include a relatively large number of pixels 404. Further, although pixels 404 are shown forming a one-dimensional array in FIG. 4, those of skill in the art will appreciate that scintillator block 402 will generally include a two-dimensional array of pixels 404.

In the exemplary embodiment, each pixel 404 includes scintillating material. When an x-ray beam 406 (i.e., generated by x-ray source 22 (shown in FIG. 1)) strikes pixel 404, the scintillating material converts x-ray beam 406 into light 408. Specifically, x-ray beam 406 travels in a transmission direction 410 until x-ray beam 406 contacts a first surface 412 of pixel 404. The scintillating material in pixel 404 converts x-ray beam 406 into light 408 that is emitted from a second, opposite surface 414 of pixel 404.

In the exemplary embodiment, detector assembly 400 includes a plurality of photodiodes 420. The number of photodiodes 420 corresponds to the number of pixels 404, such that each pixel 404 has an associated photodiode 420. Accordingly, as described above with respect to pixels 404, those of skill in the art will appreciate that detector assembly 400 will generally include a relatively large number of photodiodes 420 arranged in a two-dimensional array.

As shown in FIG. 4, a light guide 422 including a plurality of light pipes 424 is coupled between scintillator block 402 and photodiodes 420. Each light pipe 424 extends between a pixel 404 and an associated photodiode 420. Light pipe 424 guides light 408 emitted from second surface 414 into photodiode 420. Photodiode 420 converts the received light 408 into electrical signals (i.e., current) for image processing (e.g., by control system 14).

Light guide 422 and light pipes 424 may be made of a rigid or flexible material. Further, in the exemplary embodiment, light guide 422 and light pipes 424 are made of a high transmissivity material, such as glass, epoxy, transparent plastic, an x-ray detecting material (e.g., a scintillator), and/or silicone materials. Light guide 422 and light pipes 424 may be coupled to scintillator block 402 and photodiodes 420 using, for example, epoxy, silicone, and/or optical greases, using external mechanical support as needed. To facilitate guiding light 408 from pixel 404 into photodiode 420, surfaces of light pipes 424 are coated with either a diffusive coating or a high reflective coating (e.g., a mirror coating). Light guide 422 may have a height 426 (i.e., the distance between scintillator block 402 and photodiodes 420) of approximately 5 to 10 millimeters (mm). Alternatively, light guide 422 may have any dimensions that enable detector assembly 400 to function as described herein. Light guide 422 may be manufactured using additive manufacturing (e.g., 3D printing), using subtracting manufacturing (e.g., machining), or using cast or injection molding. In embodiments where light guide 422 is additively manufactured, the diffusive coating may be integrated into the assembly of light guide 422.

As shown in FIG. 4, each pixel 404 has a first cross-sectional area 430 taken substantially perpendicular to transmission direction 410, and each photodiode 420 has a second cross-sectional area 432 taken substantially perpendicular to transmission direction 410. In the exemplary embodiment, first cross-sectional area 430 is larger than second cross-sectional area 432. Accordingly, each pixel 404 has a larger footprint than each photodiode 420, and the array of pixels 404 has a larger footprint than the array of photodiodes 420. The ratio of first cross-sectional area 430 to second cross-sectional area 432 may be, for example, 4:1. Alternatively, the ratio of first cross-sectional area 430 to second cross-sectional area 432 may be any value that enables detector assembly 400 to function as described herein. Because second cross-sectional area 432 is smaller than first cross-sectional area 430, detector assembly 400 does not require manufacturing custom diodes that match the dimensions of pixels 404, reducing costs associated with manufacturing detector assembly 400.

To accommodate first and second cross-sectional areas 430 and 432, each light pipe 424 in light guide 422 transitions from first cross-sectional area 430 to second cross-sectional area 432. In the exemplary embodiment, each light pipe 424 has a relatively smooth (i.e., gradual) transition between first cross-sectional area 430 and second cross-sectional area 432.

In the exemplary embodiment, pixels 404 and photodiodes 420 are cuboids, such that first and second cross-sectional areas 430 and 432 are square. Alternatively, pixels 404 and photodiodes 420 may have any geometric shape that enables detector assembly 400 to function as described herein.

Photodiodes 420 are coupled to a substrate 440 in the exemplary embodiment. Substrate 440 includes electrical connections (not shown) for relaying electrical signals from photodiodes 420 to control system 14 (shown in FIG. 2). In the exemplary embodiment, photodiodes 420 are adjacent to one another on substrate 440. Accordingly, photodiodes 420 form a multi-diode pack 450 having a continuous array of photodiodes 420. Alternatively, photodiodes 420 may be spaced apart from one another.

Figure 5:
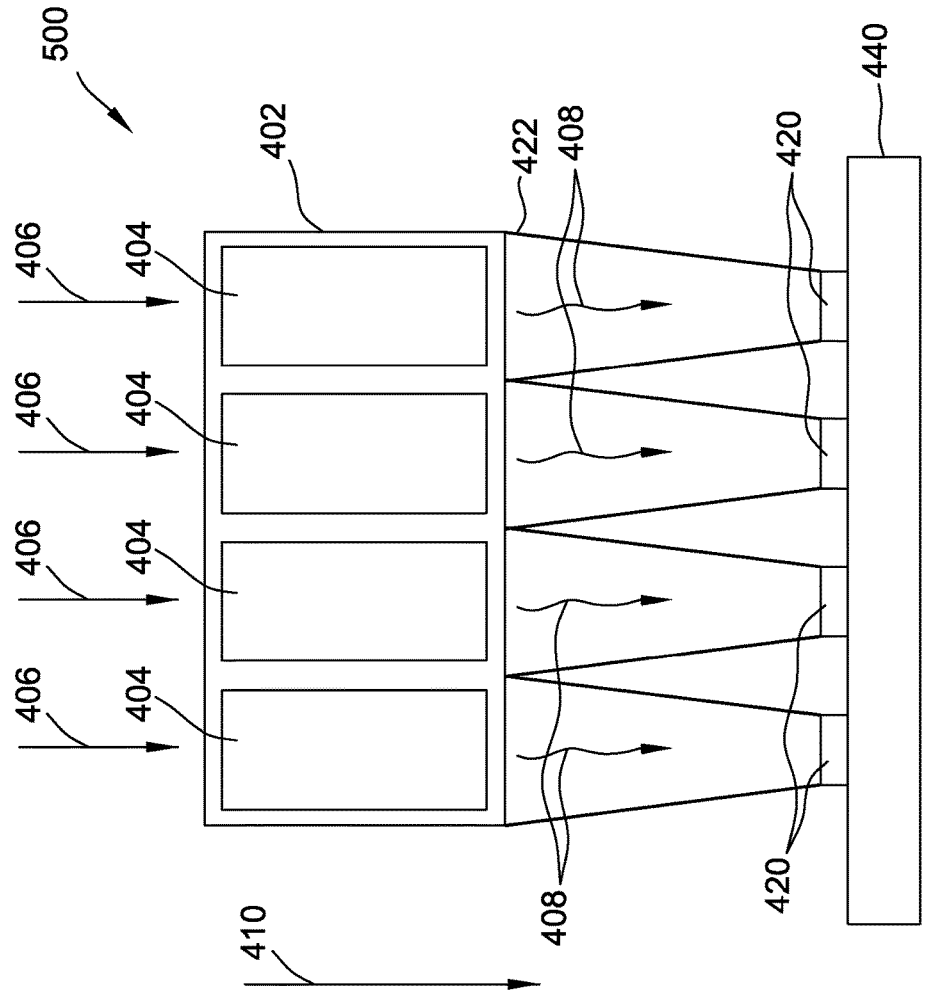
FIG. 5 is a schematic diagram of an alternative detector assembly that may be used with the CT imaging system shown in FIG. 1.

For example, FIG. 5 is a schematic diagram of an alternative embodiment of a detector assembly 500 that may be used with CT imaging system 10 (shown in FIG. 1). In FIGS. 4 and 5, like reference numerals are used to denote like components. As shown in FIG. 5, in the alternative embodiment, photodiodes 420 are spaced apart from each other such that each photodiode is substantially centered with respect to the corresponding pixel 404. Accordingly, in contrast to detector assembly 400, light pipes 424 in detector assembly 500 all have substantially the same geometry, whereas light pipes 424 in detector assembly 400 have different geometries from one another.

Figure 6:
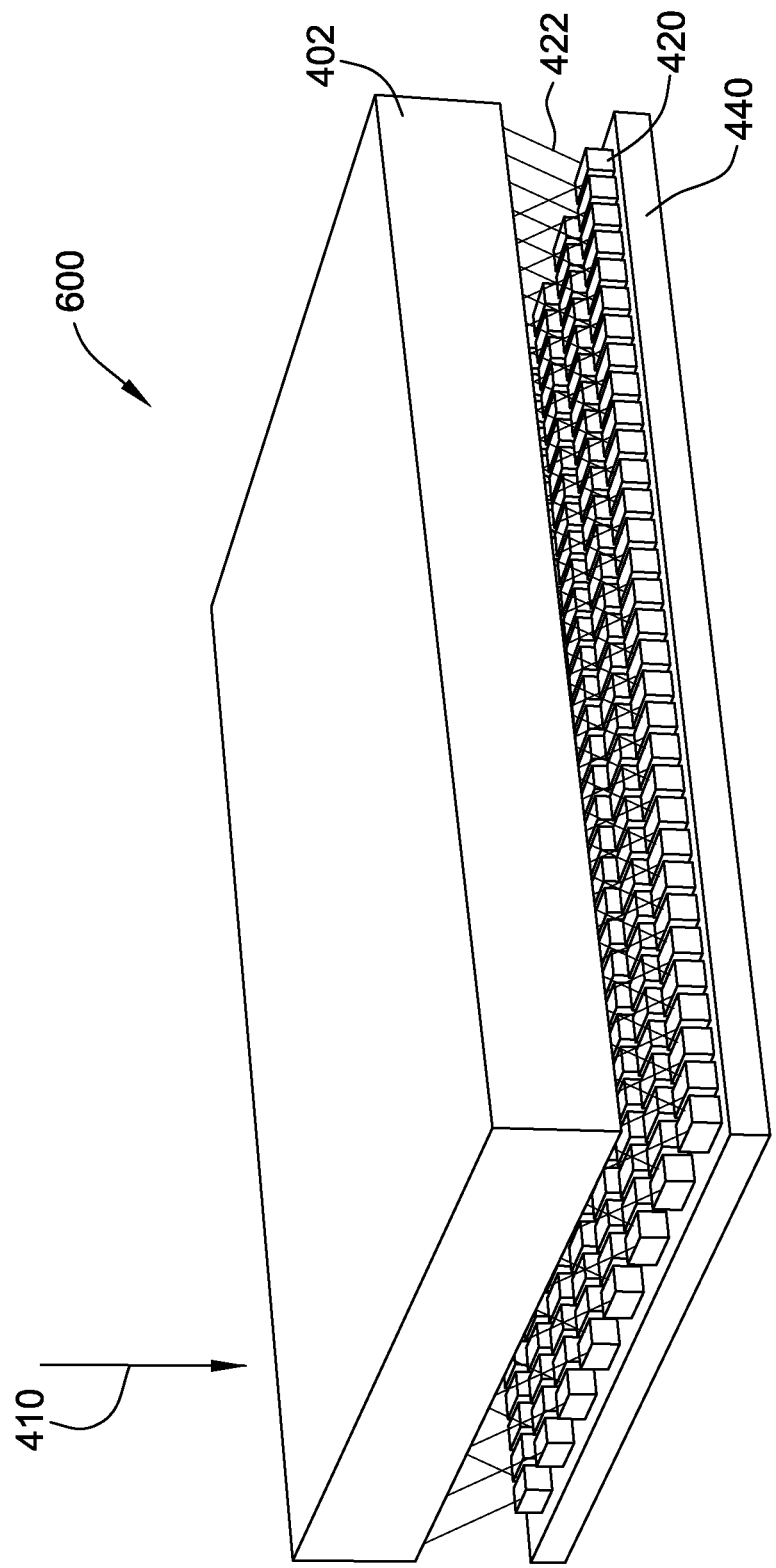
FIG. 6 is a perspective view of an exemplary detector assembly.

FIG. 6 is a perspective view of an exemplary detector assembly 600 generated by expanding detector assembly 500 to include two-dimensional arrays of pixels 404 and photodiodes 420. In FIGS. 5 and 6, like reference numerals are used to denote like components. In the embodiment shown in FIG. 6, detector assembly includes 256 pixels 404 and 256 corresponding photodiodes 420, each arranged in an 8×32 array. Alternatively, detector assembly 600 may include any arrangement of pixels 404 and photodiodes 420 that enables detector assembly 600 to function as described herein.

The embodiments described herein provide a detector assembly for a CT imaging system. The detector assembly includes a scintillator block including a plurality of pixels. Each pixel is configured to receive x-ray beams travelling in a transmission direction. The detector assembly further includes a plurality of photodiodes, and a light guide coupled between the scintillator block and the plurality of photodiodes. Each pixel has a first cross-sectional area and each photodiode has a second cross-sectional area. The first cross-sectional area is larger than the second cross-sectional area.

The systems and methods described herein may be used to detect contraband. As used herein, the term "contraband" refers to illegal substances, explosives, narcotics, weapons, special nuclear materials, dirty bombs, nuclear threat materials, a threat object, and/or any other material that a person is not allowed to possess in a restricted area, such as an airport. Contraband may be hidden within a subject (e.g., in a body cavity of a subject) and/or on a subject (e.g., under the clothing of a subject). Contraband may also include objects that can be carried in exempt or licensed quantities intended to be used outside of safe operational practices, such as the construction of dispersive radiation devices.

A computer, such as those described herein, includes at least one processor or processing unit and a system memory. The computer typically has at least some form of computer readable media. By way of example and not limitation, computer readable media include computer storage media and communication media. Computer storage media include volatile and nonvolatile, removable and non-removable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Exemplary embodiments of methods and systems are described above in detail. The methods and systems are not limited to the specific embodiments described herein, but rather, components of systems and/or steps of the methods may be used independently and separately from other components and/or steps described herein. Accordingly, the exemplary embodiment can be implemented and used in connection with many other applications not specifically described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A detector assembly for a CT imaging system, said detector assembly comprising:
   a scintillator block comprising a plurality of pixels, each pixel configured to receive x-ray beams travelling in a transmission direction;
   a plurality of photodiodes; and
   a light guide coupled between said scintillator block and said plurality of photodiodes, said light guide comprising a plurality of light pipes, each light pipe configured to guide light emitted from a single pixel of said plurality of pixels into an associated photodiode of said plurality of photodiodes, wherein each pixel has a first cross-sectional area that is substantially perpendicular to the transmission direction, wherein each photodiode has a second cross-sectional area that is substantially perpendicular to the transmission direction, wherein the first cross-sectional area is different from the second cross-sectional area, wherein each light pipe extends from a first end of said light guide to a second end of said light guide, wherein at said first end, each light pipe has a first end cross-sectional area that is substantially equal to the first cross-sectional area of the corresponding single pixel, wherein, at said second end, each light pipe has a second end cross-sectional area that is substantially equal to the second cross-sectional area of each photodiode, and wherein, for each light pipe, the first end cross-sectional area is substantially centered with the second end cross-sectional area along the transmission direction.

2. A detector assembly in accordance with claim 1, wherein said plurality of photodiodes are arranged adjacent one another to form a continuous array.

3. A detector assembly in accordance with claim 1, wherein said plurality of photodiodes are spaced apart from one another.

4. A detector assembly in accordance with claim 1, wherein said light guide is made of one of glass, epoxy, transparent plastic, an x-ray detecting material, and silicone.

5. A detector assembly in accordance with claim 1, wherein a distance between said scintillator block and said plurality of photodiodes is approximately 5 to 10 millimeters.

6. A detector assembly in accordance with claim 1, wherein surfaces of said plurality of light pipes are coated with one of a diffusive coating and a reflective coating.

7. A detector assembly in accordance with claim 1, wherein a ratio of the first cross-sectional area to the second cross-sectional area is approximately 4:1.

8. A light guide for use in a CT imaging system, said light guide coupled between a scintillator block and a plurality of photodiodes, said light guide comprising a plurality of light pipes extending from a first end of said light guide to a second end of said light guide, wherein at said first end, each light pipe of said plurality of light pipes has a first cross-sectional area that is substantially equal to and that aligns with a cross-sectional area of a corresponding single pixel in the scintillator block, wherein at said second end, each light pipe has a second cross-sectional area that is substantially equal to and that aligns with a cross-sectional area of a corresponding photodiode, wherein the first cross-sectional area is different from the second cross-sectional area, and wherein, for each light pipe, the first cross-sectional area is substantially centered with the second cross-sectional area along a light transmission direction.

9. A light guide in accordance with claim 8, wherein the first cross-sectional area is larger than the second cross-sectional area.

10. A light guide in accordance with claim 8, wherein each light pipe gradually transitions between the first and second cross-sectional areas.

11. A light guide in accordance with claim 8, wherein said light guide is made of one of glass, epoxy, transparent plastic, an x-ray detecting material, and silicone.

12. A light guide in accordance with claim 8, wherein a distance between said first end and said second end is approximately 5 to 10 millimeters.

13. A light guide in accordance with claim 8, wherein surfaces of said plurality of light pipes are coated with one of a diffusive coating and a reflective coating.

14. A light guide in accordance with claim 8, wherein a ratio of the first cross-sectional area to the second cross-sectional area is approximately 4:1.

15. A method of assembling a detector assembly for use in a CT imaging system, said method comprising:
- coupling a light guide to a scintillator block that includes a plurality of pixels, wherein each pixel is configured to receive x-ray beams travelling in a transmission direction; and
- coupling a plurality of photodiodes to the light guide, wherein the light guide includes a plurality of light pipes each configured to guide light emitted from one single pixel of the plurality of pixels into one associated photodiode of the plurality of photodiodes, wherein each pixel has a first cross-sectional area that is substantially perpendicular to the transmission direction, wherein each photodiode has a second cross-sectional area that is substantially perpendicular to the transmission direction, wherein the first cross-sectional area is larger than the second cross-sectional area, wherein each light pipe extends from a first end of the light guide to a second end of the light guide, wherein at the first end, each light pipe has a first end cross-sectional area that is substantially equal to the first cross-sectional area of the corresponding single pixel, wherein, at the second end, each light pipe has a second end cross-sectional area that is substantially equal to the second cross-sectional area of each photodiode, and wherein, for each light pipe, the first end cross-sectional area is substantially centered with the second end cross-sectional area along the transmission direction.

16. A method in accordance with claim 15, wherein coupling a plurality of photodiodes comprises coupling a plurality of photodiodes that are spaced apart from one another.

17. A method in accordance with claim 15, wherein coupling a light guide comprises coupling a light guide made of one of glass, epoxy, transparent plastic, an x-ray detecting material, and silicone.

18. A method in accordance with claim 15, further comprising coating surfaces of the plurality of light pipes with one of a diffusive coating and a reflective coating.

19. A method in accordance with claim 15, wherein coupling a plurality of photodiodes comprises coupling a plurality of photodiodes such that a ratio of the first cross-sectional area to the second cross-sectional area is approximately 4:1.

* * * * *